United States Patent
Brugger

(10) Patent No.: US 9,945,829 B2
(45) Date of Patent: Apr. 17, 2018

(54) DEEP-FRYING DEVICE, PORTABLE DEEP-FRYING OIL MEASURING DEVICE, DEEP-FRYING DEVICE SET AND METHOD FOR MONITORING A DEEP-FRYING DEVICE

(75) Inventor: Simon Brugger, Lenzkirch (DE)

(73) Assignee: Testo AG, Lenzkirch (DE)

( * ) Notice: Subject to any disclaimer, the term of this patent is extended or adjusted under 35 U.S.C. 154(b) by 419 days.

(21) Appl. No.: 14/386,204

(22) PCT Filed: Mar. 21, 2012

(86) PCT No.: PCT/EP2012/001303
§ 371 (c)(1),
(2), (4) Date: Sep. 18, 2014

(87) PCT Pub. No.: WO2013/139354
PCT Pub. Date: Sep. 26, 2013

(65) Prior Publication Data
US 2015/0027205 A1   Jan. 29, 2015

(51) Int. Cl.
*A47J 37/12* (2006.01)
*G01N 27/00* (2006.01)
*G01N 33/03* (2006.01)
*G01M 99/00* (2011.01)

(52) U.S. Cl.
CPC .............. *G01N 33/03* (2013.01); *A47J 37/12* (2013.01); *A47J 37/1266* (2013.01); *G01M 99/005* (2013.01); *G01N 27/00* (2013.01)

(58) Field of Classification Search
CPC ........ A47J 37/12; A47J 37/1266; G01N 33/03

USPC ........................................................ 73/53.01
See application file for complete search history.

(56) References Cited

U.S. PATENT DOCUMENTS

| 5,818,731 A * | 10/1998 | Mittal ................. A47J 37/1266 702/22 |
| 6,223,589 B1 * | 5/2001 | Dickert ................. G01N 11/16 310/311 |
| 2006/0272415 A1 * | 12/2006 | Liu ..................... A47J 37/1266 73/592 |

(Continued)

FOREIGN PATENT DOCUMENTS

| EP | 1439388 | 7/2004 |
| EP | 2221611 | 8/2010 |

*Primary Examiner* — Walter L Lindsay, Jr.
*Assistant Examiner* — Philip Marcus T Fadul
(74) *Attorney, Agent, or Firm* — Volpe and Koenig, P.C.

(57) ABSTRACT

According to the invention for a deep-frying device (2) including a stationary deep-frying oil sensor (5) which immerses into deep-frying oil (4) of a deep-frying oil basin (3), in order to monitor the stationary deep-frying oil sensor (5), a receiving unit (17) having a receiving data interface (8) is provided, via which interface a reference value obtained beforehand by a portable deep-frying oil measuring device (14), the portable deep-frying oil sensor (15) of which is immersed into the deep-frying oil (4) in the deep-frying oil basin (3) for measuring, can be transmitted in order to adapt a characteristic curve stored in the stationary evaluation unit (6) of the deep-frying device (2) such that the stationary evaluation unit (6) calculates a value for an evaluation variable for characterizing the deep-frying oil (4), this value being consistent with the reference value of the portable deep-frying oil measuring device (14).

23 Claims, 1 Drawing Sheet

(56) References Cited

U.S. PATENT DOCUMENTS

2006/0288877 A1    12/2006  Chambon et al.
2009/0251126 A1*  10/2009  Ishino ................ G01N 33/2852
                                                             324/71.1

* cited by examiner

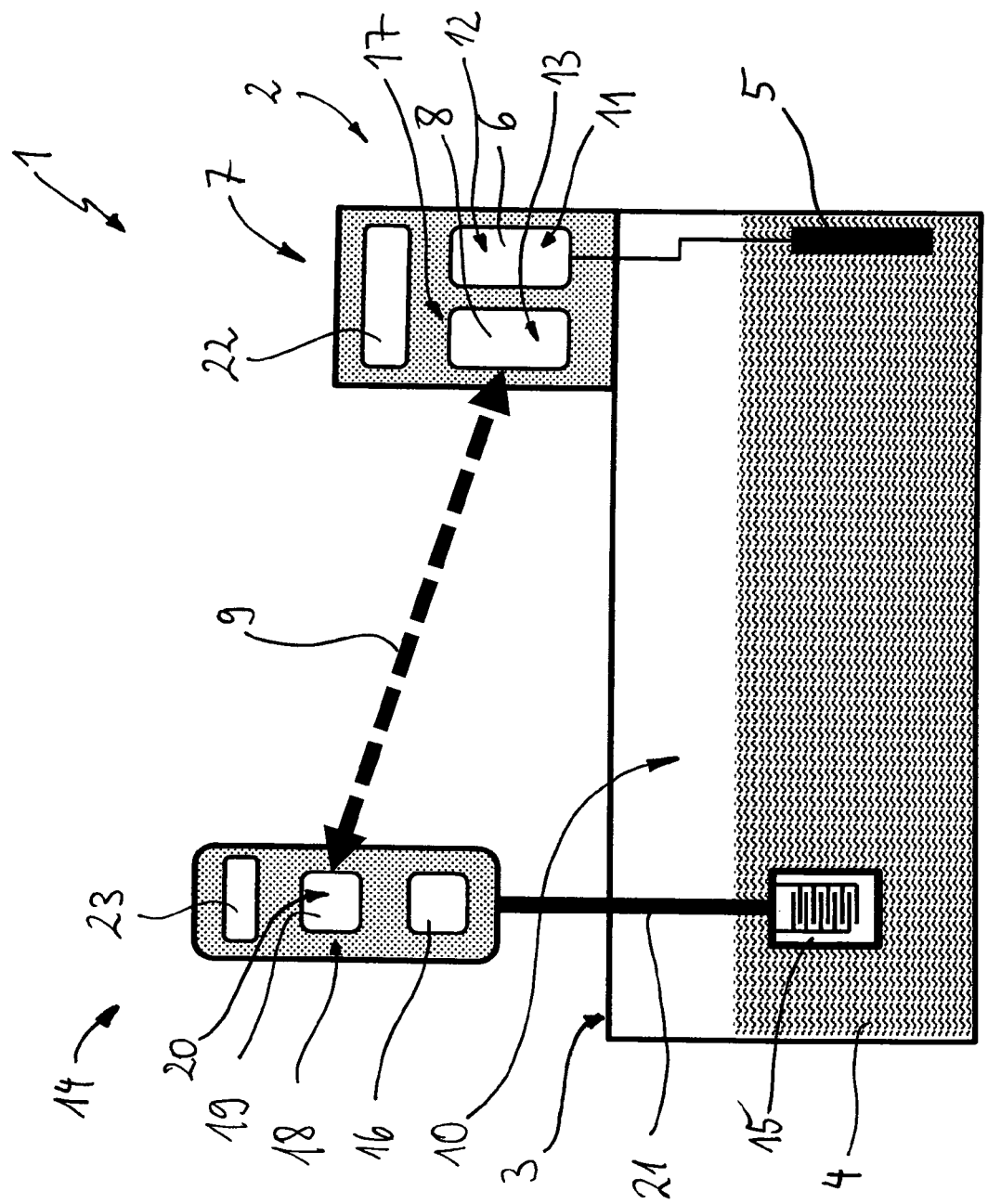

DEEP-FRYING DEVICE, PORTABLE DEEP-FRYING OIL MEASURING DEVICE, DEEP-FRYING DEVICE SET AND METHOD FOR MONITORING A DEEP-FRYING DEVICE

BACKGROUND

The invention relates to a deep-frying device having a deep-frying oil basin which is set up to accommodate deep-frying oil, a stationary deep-frying oil sensor which is set up to measure an electrical property of the deep-frying oil accommodated in the deep-frying oil basin, and a stationary evaluation unit which is connected to the stationary deep-frying oil sensor and can be used to automatically convert a measurement signal from the stationary deep-frying oil sensor into an evaluation variable for characterizing the deep-frying oil by means of at least one characteristic curve stored in the stationary evaluation unit.

The invention also relates to a portable deep-frying oil measuring device having a portable deep-frying oil sensor which is designed to be immersed into a deep-frying oil basin filled with deep-frying oil, and a portable evaluation unit which is connected to the portable deep-frying oil sensor and can be used to automatically convert a measurement signal from the portable deep-frying oil sensor into an evaluation variable for characterizing the deep-frying oil by means of at least one characteristic curve stored in the portable evaluation unit.

The invention also relates to a deep-frying device set.

The invention finally relates to a method for monitoring a deep-frying device of the type described at the outset, the deep-frying device having a stationary deep-frying oil sensor which is set up to measure an electrical property of a deep-frying oil accommodated in a deep-frying oil basin of the deep-frying device, and a measurement signal from the stationary deep-frying oil sensor being able to be automatically converted into an evaluation variable for characterizing the deep-frying oil in a stationary evaluation unit connected to the stationary deep-frying oil sensor by means of at least one characteristic curve stored in the stationary evaluation unit.

Deep-frying devices of the type described are known and are used, as so-called deep fryers, to deep-fry food. The stationary deep-frying oil sensor is used to determine the degree of staleness of the deep-frying oil used. This degree of staleness can be given, for example, by the evaluation variable % TPM (Total Polar Materials) or % FFA (free fatty acids).

Each stationary deep-frying oil sensor must be individually adjusted after the production process. This is ideally carried out in the medium of oil.

In addition, a stationary deep-frying oil sensor must be calibrated or adjusted at regular intervals due to ageing, contamination, geometrical change or damage in order to provide reliable measured values during use. If these calibrations or adjustments are not carried out, measurement errors which impair the correct function of the deep-frying device result during measurement with the deep-frying oil sensor.

U.S. Pat. No. 5,818,731 A discloses a method and an apparatus for measuring the quality of frying/cooking oil/fat, in which a single deep-frying oil sensor is arranged in a stationary manner in a deep-frying oil, in which case different types of oil and products can be set using rotary knobs.

EP 2 221 611 A1 discloses a system for monitoring the quality of cooking oil, in which measured values can be transmitted to a data collection system via a radio link.

SUMMARY

The invention is based on the object of simplifying the monitoring of the correct function of a deep-frying device.

A deep-frying device of the type described at the outset is provided, and the invention provides for at least one reference point to be defined or to be able to be defined in the at least one characteristic curve, and for a receiving unit to be formed and to provide a receiving data interface for receiving a reference value for the reference point. In this case, it is advantageous that the at least one stored characteristic curve can be automatically compared in this manner and the correct function of the stationary deep-frying oil sensor can therefore be monitored. In particular, a large number of deep-frying devices can thus be monitored in a comparatively short time. Owing to the short time needed to transmit a reference value to the deep-frying device, the monitoring can also be carried out in considerably shortened intervals of time. This simplifies the monitoring of the correct function of the deep-frying device.

One refinement of the invention may provide for the stationary deep-frying oil sensor to be arranged in an accommodating space of the deep-frying oil basin for the deep-frying oil. In this case, it is advantageous that the stationary deep-frying oil sensor can be used to determine the degree of staleness and/or the quality of the deep-frying oil used during operation of the deep-frying device.

Provision may be made for the stationary deep-frying oil sensor to be fastened to the deep-frying oil basin. This improves the usage properties of the deep-frying device since the stationary deep-frying oil sensor cannot be lost.

The data interface may be designed for wired data transmission of the reference value. However, it is particularly favorable if the receiving data interface is set up for wireless data transmission. For example, data transmission by radio, by infrared radiation, inductive data transmission, capacitive data transmission or another form of data transmission may be set up. In this case, it is advantageous that the deep-frying device can be cleaned better.

One refinement of the invention may provide for the reference value to be able to be received during measurement operation of the stationary evaluation unit. In this case, it is advantageous that the correct function of the deep-frying device can be monitored during normal operation.

One refinement of the invention may provide for each point of the at least one characteristic curve to be able to be used or defined as a reference point. In this case, it is advantageous that the correct function can be monitored independently of the properties of the deep-frying oil which has been poured in and independently of other operating conditions. It is therefore possible to dispense with using a standardized reference deep-frying oil at a predefined temperature.

Provision may be made for the reference point to be defined by the current measurement signal from the stationary deep-frying oil. This makes it possible to monitor the correct function of the deep-frying device and, in particular, of the stationary deep-frying oil sensor in a particularly simple manner during operation.

One refinement of the invention may provide for a comparison unit to be formed and to be set up to generate a warning signal if the reference value deviates from a value of the stored characteristic curve at the reference point by at least one tolerance value. Alternatively or additionally, provision may be made for a comparison unit to be formed and to be set up to generate a warning signal if the reference value deviates from a value of the evaluation variable, formed from a measurement signal from the stationary deep-frying oil sensor, by at least one tolerance value. Therefore, an incorrect function of the stationary deep-frying oil sensor can be easily and directly detected and indicated or output.

One refinement of the invention may provide for the at least one characteristic curve to be stored such that it can be modified. In this case, it is advantageous that a temporal change in the functional properties of the stationary deep-frying oil sensor can be easily compensated for in the stationary evaluation unit by modifying the at least one characteristic curve in such a manner that the original measuring behavior of the stationary deep-frying oil sensor results at least approximately or even exactly.

One refinement of the invention may provide for the stationary evaluation unit to have a means for modifying the at least one stored characteristic curve, which means can be used to modify the at least one characteristic curve in such a manner that a characteristic curve value of the modified at least one characteristic curve at the reference point is the same as the reference value. In this case, it is advantageous that changes to the stationary deep-frying oil sensor due to ageing processes or mechanical changes can be automatically compensated for.

One refinement of the invention may provide for the stationary deep-frying oil sensor and/or the stationary evaluation unit to be set up for operation at different operating frequencies of the stationary deep-frying oil sensor. In this case, it is advantageous that multi-frequency measurements of the frequency-dependent permittivity can be carried out by approaching a different operating frequency. This makes it possible to improve the accuracy with which the deep-frying oil is characterized.

In this case, provision may be made for a plurality of characteristic curves assigned to different operating frequencies of the stationary deep-frying oil sensor to be stored for use in the stationary evaluation unit. It is therefore possible to carry out frequency-dependent evaluations of output signals from the stationary deep-frying oil sensor.

One refinement of the invention may provide for the stationary deep-frying oil sensor to be able to be used to measure a physical variable dependent on the permittivity of the deep-frying oil. The real part and/or the imaginary part and/or the magnitude of the permittivity is/are preferably measured capacitively or in another manner at a predefined frequency. It is therefore possible to easily determine the degree of staleness of the deep-frying oil used.

For example, provision may be made here for the stationary deep-frying oil sensor to be in the form of a capacitive measuring sensor.

In order to be able to receive the reference value if required, provision may be made for the deep-frying device to have a means for setting up a data connection via the data interface.

In order to achieve the object in a portable deep-frying oil measuring device of the type mentioned at the outset, the invention provides for a transmitting unit to be formed and to provide a transmitting data interface for transmitting a reference value formed from the measurement signal from the portable deep-frying oil sensor as an evaluation variable during the conversion. In this case, it is advantageous that the portable deep-frying oil measuring device provides an independent measurement which can be used to monitor the correct function of the deep-frying device and of the stationary deep-frying oil sensor of the deep-frying device.

One refinement of the invention may provide for the portable deep-frying oil sensor to be able to be used to measure a physical variable dependent on the permittivity of the deep-frying oil, in particular for the portable deep-frying oil sensor to be in the form of a capacitive sensor. In this case, it is advantageous that the portable deep-frying oil sensor can be used to obtain a statement on the degree of staleness of the deep-frying oil used, which degree of staleness can be used as a reference value for monitoring the correct function of the deep-frying device.

One refinement of the invention may provide for the portable deep-frying oil sensor to be fastened to the portable evaluation unit via a rod-shaped connection element. In this case, it is advantageous that the portable deep-frying oil sensor can be easily immersed into hot deep-frying oil without the portable evaluation unit being damaged.

In order to be able to initiate a monitoring operation in a deep-frying device, provision may be made for the portable deep-frying oil measuring device to have a means for setting up a data connection via the transmitting data interface.

One refinement of the invention may provide for the portable deep-frying oil sensor and/or the portable evaluation unit to be set up for operation at different operating frequencies of the portable deep-frying oil sensor. In this case, it is advantageous that multi-frequency measurements of the frequency-dependent permittivity can be carried out by approaching different operating frequencies. This makes it possible to improve the accuracy with which the deep-frying oil is characterized.

In this case, provision may be made for a plurality of characteristic curves assigned to different operating frequencies of the portable deep-frying oil sensor to be stored for use in the portable evaluation unit. It is therefore possible to carry out frequency-dependent evaluations of output signals from the portable deep-frying oil sensor. The approachable operating frequencies are preferably matched to the approachable operating frequencies of the stationary deep-frying oil measuring device. In this case, the data connection may be set up to transmit a frequency-dependent reference value.

In order to achieve the stated object, a deep-frying device set has, according to the invention, a deep-frying device according to the invention, in particular as described above, and a portable deep-frying oil measuring device according to the invention, in particular as described above, the receiving data interface of the deep-frying device being designed to appropriately transmit the reference value to the transmitting data interface of the portable deep-frying oil measuring device. In this case, it is advantageous that the deep-frying device set has two mutually independent possible ways of determining the degree of staleness of the deep-frying oil, which can be and are compared with one another for the purpose of monitoring.

One refinement of the invention may provide for the at least one characteristic curve stored in the deep-frying device to be able to be converted into the at least one characteristic curve stored in the portable deep-frying oil measuring device by means of an offset shift. In this case, it is advantageous that the at least one characteristic curve can be modified in the deep-frying device in a particularly simple manner by means of an offset shift.

One refinement of the invention may provide for the stationary deep-frying oil sensor and the portable deep-frying oil sensor to operate according to the same physical measurement principle. For example, provision may be made for the stationary deep-frying oil sensor and the portable deep-frying oil sensor to be set up to measure the same physical variable or physical variables which can be compared with one another. In this case, it is advantageous that the correct function of the stationary deep-frying oil sensor can be monitored in a particularly simple manner by comparing measured values with the portable deep-frying oil sensor.

In order to achieve the stated object in a method of the type described at the outset, the invention provides for a portable deep-frying oil sensor of a portable deep-frying oil measuring device to be immersed into the deep-frying oil, for a measurement signal from the portable deep-frying oil sensor to be converted into a reference value for an evaluation variable for characterizing the deep-frying oil, for the reference value to be transmitted to the stationary evaluation unit of the deep-frying device via at least one data interface, for the reference value to be compared with a value of the at least one characteristic curve stored in the stationary evaluation unit, and for a deviation of the value from the reference value to be automatically determined. In this case, it is advantageous that the correct function of the deep-frying device, in particular of the stationary deep-frying oil sensor, can be automatically monitored in a simple manner by means of an independent measurement using the portable deep-frying oil measuring device.

One refinement of the invention may provide for the value of the at least one characteristic curve stored in the stationary evaluation unit to be derived from a measurement signal from the stationary deep-frying oil sensor. In this case, it is advantageous that the correct function of the deep-frying device can be monitored during operation by comparing the reference value obtained using the portable deep-frying oil sensor with the instantaneous value of the instantaneous measurement signal from the stationary deep-frying oil sensor.

Provision is preferably made for the portable deep-frying oil sensor and the stationary deep-frying oil sensor to measure the same deep-frying oil during the method. It is particularly favorable if the respective measuring operations are carried out at the same time.

Provision may be made for a warning signal to be generated if the deviation is greater than a tolerance value. In this case, it is advantageous that an unacceptable, incorrect function of the stationary deep-frying oil sensor can be detected and indicated or output.

One refinement of the invention may provide for the at least one characteristic curve stored in the stationary evaluation unit to be modified until the deviation of a value of the evaluation variable, which is derived or formed from the measurement signal from the stationary deep-frying oil sensor using the modified at least one characteristic curve, from the reference value is less than a predefined threshold value. This modification is preferably carried out automatically. In this case, it is advantageous that the stationary deep-frying oil sensor and the stationary evaluation unit can be adjusted easily and even automatically in order to monitor or even restore a defined method of operation of the deep-frying device.

Provision is preferably made for the threshold value to be less than the tolerance value. The threshold value may also be zero, with the result that the at least one characteristic curve is modified until the reference value is equal to the derived value for the modified at least one characteristic curve.

Provision may be made for the at least one characteristic curve stored in the stationary evaluation unit to be modified by means of an offset shift. In this case, it is advantageous that it is possible to carry out a particularly simple form of the modification in which only one parameter for the offset shift is varied.

It is particularly favorable if a deep-frying device according to the invention and/or a portable deep-frying oil measuring device according to the invention is/are used in the method according to the invention. If both a deep-frying device according to the invention and a portable deep-frying oil measuring device according to the invention are used, even the advantages of using a deep-frying device set according to the invention in the method according to the invention result.

BRIEF DESCRIPTION OF THE DRAWINGS

The invention is now described in more detail using an exemplary embodiment but is not restricted to the exemplary embodiment. Further exemplary embodiments result from combining individual or a plurality of features of the claims with one another and/or with individual or a plurality of features of the exemplary embodiment.

The only FIGURE,

FIG. 1 shows a deep-frying device set according to the invention in a highly schematic illustration for explaining the method according to the invention.

DETAILED DESCRIPTION OF THE PREFERRED EMBODIMENTS

A deep-frying device set which is denoted 1 as a whole has a deep-frying device 2 for deep-frying food.

For this purpose, the deep-frying device 2 has a deep-frying oil basin 3 in which the deep-frying oil 4 is accommodated during use.

The food is therefore deep-fried by being immersed into the deep-frying oil 4 in the deep-frying oil basin 3, the deep-frying oil 4 having been previously heated using a heating device known per se (not illustrated any further).

In order to monitor the state of the deep-frying oil 4, a stationary deep-frying oil sensor 5 is provided and can be used to measure the permittivity of the deep-frying oil 4 as an electrical property. In this case, the stationary deep-frying oil sensor 5 can measure the real part or the imaginary part or the magnitude or another combination of the real part and imaginary part of the permittivity.

It is known that the deep-frying oil 4 changes after a certain usage time in such a manner that a change in the electrical properties can be measured. The stationary deep-frying oil sensor 5 can therefore be used to detect whether the deep-frying oil 4 must be replaced.

For this purpose, the stationary deep-frying oil sensor 5 is connected to a stationary evaluation unit 6 which can be used to record and evaluate the measurement signals from the stationary deep-frying oil sensor 5.

For the purpose of evaluation, at least one characteristic curve is stored in the stationary evaluation unit 6, which characteristic curve can be used to convert the measurement signal from the stationary deep-frying oil sensor 5 into an evaluation variable for characterizing the deep-frying oil 4. A value for the evaluation variable is therefore derived or formed from the measurement signal in the stationary evaluation unit 6. In the exemplary embodiment, this is a statement of the proportion of polar components in the deep-frying oil 4. It is known that this proportion of electrically polar components increases with increasing usage duration of the deep-frying oil 4, with the result that it is necessary to replace the deep-frying oil 4 with new deep-frying oil as of a particular percentage proportion of such polar components (TPM).

The measurement signal from the stationary deep-frying oil sensor 5 defines a reference point in the characteristic curve at which the current evaluation variable for characterizing the deep-frying oil 4 is taken.

The stationary evaluation unit 6 is in the form of part of a stationary deep-frying oil measuring device 7. The stationary deep-frying oil measuring device 7 is fastened or connected to the deep-frying oil basin 3.

A receiving unit 17 with a receiving data interface 8 is also formed on the stationary deep-frying oil measuring device 7 of the deep-frying device 2. The receiving data interface 8 can be used to receive a reference value via a data connection 9. This reference value is received during measurement operation of the stationary evaluation unit 6.

As already mentioned the stationary deep-frying oil measuring device 7 is fixedly or releasably connected to the deep-frying oil basin 3.

The stationary deep-frying oil sensor 5 is arranged in the receiving space 10 of the deep-frying oil basin 3 for the deep-frying oil 4 in such a manner that the stationary deep-frying oil sensor 5—as shown in FIG. 1—is immersed into the deep-frying oil 4 during normal filling of the deep-frying oil basin 3. In this case, the stationary deep-frying oil sensor 5 is releasably or fixedly fastened in the deep-frying oil basin 3. For example, the deep-frying oil sensor 5 may be fitted to the supply line of a heater.

The receiving data interface 8 may be set up for wired and/or wireless data transmission. The situation in which wireless data transmission can be carried out via the data connection 9 using Bluetooth or another protocol is shown in FIG. 1.

A comparison unit 11 is formed in the stationary evaluation unit 6 and can be or is used to compare the received reference value with the value of the evaluation variable for characterizing the deep-frying oil 4, which value was formed previously or in a temporally parallel manner from the measurement signal from the stationary deep-frying oil sensor 5.

The stationary evaluation unit 6 is set up assuming that, during correct operation of the stationary deep-frying oil measuring device 7, the received reference value is supposed to correspond to the value formed. However, the function of the stationary deep-frying oil sensor 5 may change over the course of time on account of contamination, ageing processes and the like, for example also damage, in such a manner that the value formed in the conversion deviates from the reference value.

If the deviation of these values from one another is greater than a predefined tolerance value, this means an incorrect function of the stationary deep-frying oil measuring device 7 and, in particular, of the associated stationary deep-frying oil sensor 5.

This can be indicated and/or output and/or logged by a warning signal which is generated in the comparison unit 11.

In the exemplary embodiment according to FIG. 1, the characteristic curve mentioned is stored in a manner such that it can be modified, with the result that the characteristic curve can be and is changed if the formed or calculated value deviates too greatly from the reference value.

For this purpose, the stationary evaluation unit 6 has a means 12 for modifying the stored characteristic curve. This can be achieved, for example, by changing or adapting parameters which describe the characteristic curve, or by means of an offset shift of characteristic curve values stored in tabular form, for example.

The means 12 for modifying the stored characteristic curve is used to modify the modified characteristic curve in such a manner that the characteristic curve value of the modified characteristic curve is the same as the received reference value at the reference point.

Since the reference point is defined by the current measurement signal from the stationary deep-frying oil sensor 5, each point of the characteristic curve can be used as a reference point and is defined as a reference point if the measurement signal from the stationary deep-frying oil sensor 5 distinguishes this point.

In a manner known per se, the stationary deep-frying oil sensor 5 is in the form of a capacitive measuring sensor which can be and is used to measure a physical variable dependent on the permittivity of the deep-frying oil 4, for example a component of this permittivity.

The stationary deep-frying oil measuring device 7 also comprises a means 13 for setting up the data connection 9.

The means 13 can be used, for example, to manually trigger the generation or transmission of a reference value which can then be received—as described—using the receiving data interface 8.

This reference value can be generated using a portable deep-frying oil measuring device which is denoted 14 as a whole.

For this purpose, the portable deep-frying oil measuring device has a portable deep-frying oil sensor 15 which is designed to be immersed into the deep-frying oil basin 3 of the stationary deep-frying device 2, which basin is filled with deep-frying oil 4.

A portable evaluation unit 16 of the portable deep-frying oil measuring device 14 is connected to this portable deep-frying oil sensor 15 and is used to read a measurement signal from the portable deep-frying oil sensor 15.

This measurement signal is converted into an evaluation variable for characterizing the deep-frying oil 4 by evaluating a characteristic curve stored in the portable evaluation unit 16.

In a manner known per se, the portable deep-frying oil sensor 15 is also in the form of a capacitive measuring sensor which can be used to measure an electrical property of the deep-frying oil 4.

The stationary deep-frying oil sensor 5 and the portable deep-frying oil sensor 15 operate according to the same physical measurement principle and are therefore set up to measure the same physical variable or at least physical variables which can be compared with one another.

The portable deep-frying oil measuring device 14 has a transmitting unit 18 which provides a transmitting data interface 19.

The transmitting data interface 19 is matched to the receiving data interface 8 of the receiving unit 17 of the stationary deep-frying oil measuring device 7 in such a manner that both interfaces define and provide the data connection 9.

After the means 13 for setting up the connection on the receiving unit 17 or a means 20 for setting up the connection on the transmitting unit 18 has been actuated, the data connection 9 is set up and the transmitting unit 18 transmits the value of the evaluation variable, which is formed from the measurement signal from the portable deep-frying oil sensor 15, to the receiving unit 17 as a reference value via the transmitting data interface 19 and the receiving data interface 8.

In this manner, the measurement using the portable deep-frying oil sensor 15 can be compared with the measurement using the stationary deep-frying oil sensor 5 in the comparison unit 11 of the stationary deep-frying oil measuring device 7 by comparing the reference value transmitted via the data connection 9 with the value of the evaluation variable for characterizing the deep-frying oil 4, which value is currently formed in the evaluation unit 6.

A deviation of these values from one another indicates different functioning of the stationary deep-frying oil measuring device 7, on the one hand, and of the portable deep-frying oil measuring device 14, on the other hand.

This different functioning can indicate, as a warning, that the correct function of the stationary deep-frying oil measuring device 7 was impaired over the course of time. This can be indicated or output by means of the warning signal already mentioned. The function of the stationary deep-frying oil measuring device 7 can be matched to the function of the portable deep-frying oil measuring device 14 by accordingly tracking the characteristic curve stored in the evaluation unit 6.

In the exemplary embodiment, this modification of the characteristic curve is carried out by means of an offset shift until the value of the evaluation variable calculated from the measurement signal from the stationary deep-frying oil sensor 5 deviates from the transmitted reference value only by a predefined threshold value which may also be zero.

It is also mentioned that the portable deep-frying oil measuring device 14 has a rod-shaped connection element 21 which is used to fasten the portable deep-frying oil sensor 15 to the portable evaluation unit 16. In this manner, the portable deep-frying oil sensor 15 can be immersed into the hot deep-frying oil 4 without the electronics of the evaluation unit 16 being damaged.

The stationary deep-frying oil measuring device 7 has a display 22 which can be used to indicate the value formed from the measurement signal from the stationary deep-frying oil sensor 5 with the aid of the stored characteristic curve and/or the previously mentioned warning signal. In addition, information relating to the data connection 9 can be indicated on the display 22.

The portable deep-frying oil measuring device 14 likewise has a display 23 which can be and is used to indicate the value calculated from the measurement signal from the portable deep-frying oil sensor 15 with the aid of the characteristic curve stored in the portable deep-frying oil measuring device 14. The portable deep-frying oil measuring device 14 can therefore also be used in a known manner as an automatic deep-frying oil measuring device. The range of functions of the portable deep-frying oil measuring device 14 can be extended to monitoring the correct function of a deep-frying device 2 by the additional, novel design and use of a transmitting unit 18 on this portable deep-frying oil measuring device 14.

In addition, the stationary deep-frying oil sensor 5 and the stationary evaluation unit 6 may be set up for operation at different operating frequencies of the stationary deep-frying oil sensor 5. Multi-frequency measurements of the frequency-dependent permittivity can therefore be carried out. For example, it is therefore possible to approach different operating frequencies of the deep-frying oil sensor 5 at which a value of the evaluation variable is then respectively determined.

For this purpose, a plurality of characteristic curves are stored for use in the stationary evaluation unit 6, which characteristic curves are each assigned to different operating frequencies of the deep-frying oil sensor 5. The characteristic curve for the instantaneous operating frequency is then automatically selected and evaluated in each case.

In a similar manner, the portable deep-frying oil sensor 15 and the portable evaluation unit 16 are set up to carry out multi-frequency measurements. This allows the characteristic curves in the stationary deep-frying oil measuring device 7 to be compared in a frequency-dependent manner with a respective associated, frequency-related reference value from the portable deep-frying oil measuring device 7.

In the deep-frying device 2 having a stationary deep-frying oil sensor 5 which is immersed into deep-frying oil 4 in a deep-frying oil basin 3, it is proposed, in order to monitor the stationary deep-frying oil sensor 5, to form a receiving unit 17 having a receiving data interface 8 which can be used to transmit a reference value previously obtained using a portable deep-frying oil measuring device 14, the portable deep-frying oil sensor 15 of which is immersed into the deep-frying oil 4 in the deep-frying oil basin 3 for measurement, in order to adapt a characteristic curve stored in the stationary evaluation unit 6 of the deep-frying device 2 in such a manner that the stationary evaluation unit 6 calculates a value for an evaluation variable for characterizing the deep-frying oil 4, which value matches the reference value from the portable deep-frying oil measuring device 14 (FIG. 1).

The invention claimed is:

1. A deep-frying device (2) comprising a deep-frying oil basin (3) which is set up to accommodate deep-frying oil (4), a stationary deep-frying oil sensor (5) which is set up to measure an electrical property of the deep-frying oil (4) accommodated in the deep-frying oil basin (3), and a stationary evaluation unit (6) which is connected to the stationary deep-frying oil sensor (5) and automatically converts a measurement signal from the stationary deep-frying oil sensor (5) into an evaluation variable for characterizing the deep-frying oil (4) by at least one characteristic curve stored in the stationary evaluation unit (6), wherein at least one reference point is defined in the at least one characteristic curve, and a receiving unit (17) is formed and provides a receiving data interface (8) for receiving a reference value for the reference point, wherein the receiving data interface (8) is set up for wireless data transmission, and the stationary evaluation unit (6) is configured for modifying the at least one stored characteristic curve to modify the at least one characteristic curve in such a manner that a characteristic curve value of the modified at least one characteristic curve at the reference point is the same as the reference value, and a plurality of characteristic curves assigned to different operating frequencies of the deep-frying oil sensor (5) are stored for use in the stationary evaluation unit (6).

2. The deep-frying device (2) as claimed in claim 1, wherein the stationary deep-frying oil sensor (5) is arranged in a receiving space (10) of the deep-frying oil basin (3) for the deep-frying oil (4).

3. The deep-frying device (2) as claimed in claim 1, wherein the stationary deep-frying oil sensor (5) is fastened in the deep-frying oil basin (3).

4. The deep-frying device (2) as claimed in claim 1, wherein the reference value is received during measurement operation of the stationary evaluation unit (6).

5. The deep-frying device (2) as claimed in claim 1, wherein each point of the at least one characteristic curve is used or defined as a reference point.

6. The deep-frying device (2) as claimed in claim 1, wherein the reference point is defined by the current measurement signal from the stationary deep-frying oil sensor (5).

7. The deep-frying device (2) as claimed in claim 1, further comprising a comparison unit (11) that is set up to generate a warning signal if the reference value deviates from a value of the stored at least one characteristic curve at the reference point or from a value of the evaluation variable, formed from a measurement signal from the stationary deep-frying oil sensor (5), by at least one tolerance value.

8. The deep-frying device (2) as claimed in claim 1, wherein the at least one characteristic curve is stored such that it is modifiable.

9. The deep-frying device (2) as claimed in claim 1, wherein the stationary deep-frying oil sensor (5) is used to measure a physical variable dependent on a permittivity of the deep-frying oil (4).

10. The deep-frying device (2) as claimed in claim 1, wherein the stationary deep-frying oil sensor (5) is a capacitive measuring sensor.

11. The deep-frying device (2) as claimed in claim 1, wherein the deep-frying device (2) has a data connection set-up device (13) that sets up a data connection (9) via the receiving data interface (8).

12. A deep-frying device set (1) having a deep-frying device (2) as claimed in claim 1, further comprising a portable deep-frying oil measuring device (14) the receiving data interface (8) of the deep-frying device (2) being designed to appropriately transmit the reference value to a transmitting data interface (19) of the portable deep-frying oil measuring device (14).

13. The deep-frying device set (1) as claimed in claim 12, wherein the stationary deep-frying oil sensor (2) and the portable deep-frying oil device (14) operate according to a same physical measurement principle or are set up to measure a same physical variable or physical variables which are comparable with one another.

14. A portable deep-frying oil measuring device (14) having a portable deep-frying oil sensor (15) which is designed to be immersed into a deep-frying oil basin (3) filled with deep-frying oil (4), and a portable evaluation unit (16) which is connected to the portable deep-frying oil sensor (15) and is used to automatically convert a measurement signal from the portable deep-frying oil sensor (15) into an evaluation variable for characterizing the deep-frying oil (4) by at least one characteristic curve stored in the portable evaluation unit (16), and a transmitting unit (18) that provides a transmitting data interface (19) for transmitting a reference value formed from the measurement signal from the portable deep-frying oil sensor (15) as an evaluation variable, and a plurality of characteristic curves assigned to different operating frequencies of the portable deep-frying oil sensor (15) are stored for use in the portable evaluation unit (16).

15. The portable deep-frying oil measuring device (14) as claimed in claim 14, wherein the portable deep-frying oil sensor (15) is used to measure a physical variable dependent on a permittivity of the deep-frying oil (4).

16. The portable deep-frying oil measuring device (14) as claimed in claim 14, wherein the portable deep-frying oil sensor (15) is fastened to the portable evaluation unit (6) via a rod-shaped connection element (21).

17. The portable deep-frying oil measuring device (14) as claimed in claim 14, wherein the portable deep-frying oil measuring device (14) has a data connection set-up device (20) that sets up a data connection (9) via the transmitting data interface (19).

18. The deep-frying device set (1) as claimed in claim 12, wherein the at least one characteristic curve stored in the deep-frying device (2) is converted into the at least one characteristic curve stored in the portable deep-frying oil measuring device (14) by an offset shift.

19. A method for monitoring a deep-frying device (2), comprising: providing the deep-frying device (2) with a stationary deep-frying oil sensor (5) which is set up to measure an electrical property of a deep-frying oil (4) accommodated in a deep-frying oil basin (3) of the deep-frying device (2), and automatically converting a measurement signal from the stationary deep-frying oil sensor (5) into an evaluation variable for characterizing the deep-frying oil (4) in a stationary evaluation unit (6) connected to the stationary deep-frying oil sensor (5) by at least one characteristic curve stored in the stationary evaluation unit (6), immersing a portable deep-frying oil sensor (15) of a portable deep-frying oil measuring device (14), which is independent of the stationary deep-frying oil sensor (5), into the deep-frying oil (4), converting a measurement signal from the portable deep-frying oil sensor (15) into a reference value for an evaluation variable for characterizing the deep-frying oil (4), transmitting the reference value to the stationary evaluation unit (6) of the deep-frying device (2) via at least one data interface (8, 19), comparing the reference value with a value of the at least one characteristic curve stored in the stationary evaluation unit (6), automatically determining a deviation of the value from the reference value, and automatically modifying the at least one characteristic curve stored in the stationary evaluation unit (6) until the deviation of a value of the evaluation variable, which is derived from the measurement signal from the stationary deep-frying oil sensor (5) using the modified at least one characteristic curve, from the reference value is less than a predefined threshold value.

20. The method as claimed in claim 19, wherein the value of the at least one characteristic curve stored in the stationary evaluation unit (6) is derived from a measurement signal from the stationary deep-frying oil sensor (5).

21. The method as claimed in claim 19, further comprising generating a warning signal if the deviation is greater than a tolerance value.

22. The method as claimed in claim 19, further comprising generating a warning signal if the deviation is greater than a tolerance value, wherein the threshold value is less than the tolerance value.

23. The method as claimed in claim 19, wherein the at least one characteristic curve stored in the stationary evaluation unit is modified by an offset shift.

* * * * *